(12) United States Patent
Piantoni et al.

(10) Patent No.: US 11,957,550 B2
(45) Date of Patent: Apr. 16, 2024

(54) APPARATUS AND METHOD FOR FORMING AN ABSORBENT PAD

(71) Applicant: GDM S.p.A., Bologna (IT)

(72) Inventors: Matteo Piantoni, Albino (IT); Valerio Soli, Bologna (IT); Marco Rosani, Vailarate (IT); Federico Toscani, Castelleone (IT); Giuseppe Poli, Cumignano sul Naviglio (IT)

(73) Assignee: GDM S.P.A., Bologna (IT)

( * ) Notice: Subject to any disclaimer, the term of this patent is extended or adjusted under 35 U.S.C. 154(b) by 1100 days.

(21) Appl. No.: 16/491,999

(22) PCT Filed: Mar. 19, 2018

(86) PCT No.: PCT/IB2018/051805
§ 371 (c)(1),
(2) Date: Sep. 6, 2019

(87) PCT Pub. No.: WO2018/172902
PCT Pub. Date: Sep. 27, 2018

(65) Prior Publication Data
US 2021/0145652 A1    May 20, 2021

(30) Foreign Application Priority Data

Mar. 22, 2017  (IT) .................... 102017000031281

(51) Int. Cl.
*A61F 13/15*        (2006.01)
*A61F 13/532*       (2006.01)

(52) U.S. Cl.
CPC .. *A61F 13/15658* (2013.01); *A61F 13/15699* (2013.01); *A61F 13/5323* (2013.01)

(58) Field of Classification Search
CPC ............ A61F 13/5323; A61F 13/15699; A61F 13/15634; A61F 13/15642; A61F 13/1565; A61F 13/15658
See application file for complete search history.

(56) References Cited

U.S. PATENT DOCUMENTS

| 5,494,622 A | 2/1996 | Heath et al. |
| 2011/0042844 A1 | 2/2011 | Brown et al. |

(Continued)

FOREIGN PATENT DOCUMENTS

| CN | 105960244 A | 9/2016 |
| EP | 1609582 B1 | 2/2008 |

(Continued)

OTHER PUBLICATIONS

Chinese Office Action dated Jul. 26, 2021 from counterpart Chinese Patent Application No. CN105960244.

(Continued)

*Primary Examiner* — Carson Gross
(74) *Attorney, Agent, or Firm* — SHUTTLEWORTH & INGERSOLL, PLC; Timothy J. Klíma

(57) ABSTRACT

A method for forming an absorbent pad including a first layer, a second layer and an absorbent material interposed between the first and the second layer and arranged according to a spreading pattern M1 having at least one channel which is free of absorbent material, includes a step of feeding a first web, intended to form the first layer of the pad; a step of feeding a second web, intended to form the second layer of the pad; a step of spreading the absorbent material on the first web according to the spreading pattern M1; a step of spreading an adhesive on the first web according to a gluing pattern; a step of welding the first web (Continued)

and the second web according to a welding pattern M3 including at least one welding zone at the channel on the pad.

15 Claims, 2 Drawing Sheets

(56) References Cited

U.S. PATENT DOCUMENTS

| | | | |
|---|---|---|---|
| 2012/0312491 A1 | 12/2012 | Jackels et al. | |
| 2013/0284361 A1* | 10/2013 | Tsujimoto | A61F 13/15617 156/276 |
| 2015/0223990 A1* | 8/2015 | Armstrong-Ostle | B32B 37/24 156/60 |
| 2016/0175169 A1* | 6/2016 | Bianchi | A61F 13/15699 604/385.101 |
| 2019/0083324 A1* | 3/2019 | Venturino | A61F 13/535 |

FOREIGN PATENT DOCUMENTS

| | | |
|---|---|---|
| EP | 2905001 A1 | 8/2015 |
| EP | 2949302 A1 | 12/2015 |
| EP | 3037079 A1 | 6/2016 |
| GB | 2257652 B | 5/1995 |
| GB | 2503529 A | 1/2014 |
| WO | 2011099297 A1 | 8/2011 |

OTHER PUBLICATIONS

International Search Report and Written Opinion dated May 15, 2018 from counterpart International Patent Application No. PCT/IB2018/051805.

Notice of Opposition dated Jun. 7, 2022 from counterpart European Patent Application No. 3600191.

Reply to Notice of Opposition dated Oct. 28, 2022 from counterpart European Patent Application No. 3600191.

Annex to Summons dated Feb. 8, 2023 from counterpart European Patent Application No. 3600191.

* cited by examiner

APPARATUS AND METHOD FOR FORMING AN ABSORBENT PAD

This application is the National Phase of International Application PCT/162018/051805 filed Mar. 19, 2018 which designated the U.S.

This application claims priority to Italian Patent Application No. 102017000031281 filed Mar. 22, 2017, which application is incorporated by reference herein.

TECHNICAL FIELD

This invention relates to an apparatus and a method for forming an absorbent structure, specifically an absorbent pad or "core", as it also known in the trade, intended for use in absorbent sanitary articles such as, for example, nappies for children and adults, to which express reference is hereinafter made without losing in generality, sanitary towels and the like.

BACKGROUND ART

As is known, nappies comprise an absorbent pad or core which is normally enclosed between a permeable inner layer of non-woven fabric and an impermeable outer layer made, for example, of polyethylene.

Absorbent pads of known type comprise an absorbent core made of an absorbent material, such as, for example, granules of superabsorbent polymer material (SAP) inside a mixture of containment cellulose pulp (fluff) and absorbent material binder, sandwiched between two layers of non-woven fabric.

To improve performance in terms of absorption, comfort and distribution of absorbed liquids, pads have been developed which are provided with longitudinal channels without absorbent material between the two layers of non-woven fabric.

Document EP2905001 relates to an apparatus and a method for making an absorbent pad of this kind.

The apparatus described comprises rollers for transferring two sheets of non-woven fabric, a system for feeding the absorbent material and configured in such a way that the aforesaid channels are formed between the layers of non-woven fabric, and a system for applying adhesive used to join the two sheets.

According to the description, the rollers feed the sheets and the adhesive is spread on the sheets even at the channels; the absorbent material is spread discretely on one of the two sheets, trying to prevent it from being deposited on the channels.

Downstream of the adhesive applicators, the apparatus comprises a pressure device to optimize adhesion of the sheets to each other at the channels. More specifically, the channels are formed when the two sheets are made to adhere to each other under the combined action of the adhesive and the pressure.

One disadvantage of this system is that the glue is spread also on the zones where the channels are to be formed and the absorbent material can thus stick to the sheets in those very zones.

The pressing action applied by the pressure device can therefore damage or even perforate the pad if absorbent material is deposited between the pressure device and the mating part opposed to it.

Moreover, to obtain a satisfactory join at the channels, the pressure applied by the pressure device must be very precisely and painstakingly calibrated in order to avoid making defective nappies.

DISCLOSURE OF THE INVENTION

In this context, the main purpose of this disclosure is to propose an apparatus for forming an absorbent pad to overcome the above mentioned disadvantages.

One aim of this disclosure is to propose an apparatus for forming an absorbent pad with channels which is more reliable than prior art solutions.

Another aim of this disclosure is to propose an apparatus for forming an absorbent pad with channels which allows making precise absorbent pads with effective channels.

These aims are fully achieved by an apparatus for forming an absorbent pad having the features resulting from the combination of one or more of the claims accompanying this application.

According to a first aspect of it, this disclosure relates to an apparatus for forming an absorbent pad for an absorbent sanitary article.

The pad comprises a first layer, a second layer and an absorbent material interposed between the first and the second layer and arranged according to a spreading pattern having at least one channel which is free of absorbent material.

According to one aspect of this disclosure, the first layer and the second layer are directly attached to each other at the first channel.

The forming apparatus comprises a forming drum, a first feed system for feeding to the forming drum a first web, intended to form the first layer, and a second feed system for feeding to the forming drum a second web, intended to form the second layer.

The forming apparatus comprises at least one spreader for spreading the absorbent material on the forming drum and the forming drum comprises a suction system to create, for example on the first web advancing on the forming drum, a spread of absorbent material according to the absorbent material spreading pattern.

According to one aspect of this disclosure, the forming drum comprises at least one insert in the suction system to inhibit suction at the channel so that absorbent material is not retained at the channel.

The forming apparatus comprises at least one adhesive dispenser located upstream of the spreader of the absorbent material in a feed direction V of the first web to apply on the first web a layer of adhesive according to a gluing pattern and intended, for example, at least to retain the absorbent material and to contribute to joining the first and second webs.

Once joined to each other, the first web, the second web and the absorbent material form a composite web which is subsequently cut into pieces to obtain the aforesaid pads.

According to one aspect of this disclosure, the apparatus comprises a welding system for welding the first web to the second web to join the first web to the second web at least at the channel without absorbent material.

According to one aspect of this disclosure, the welding system comprises a first welding element and a second welding element acting in conjunction with each other.

The first welding element has an opposing surface for contact with the second welding element and shaped according to a welding pattern which comprises at least one welding zone at the channel.

The weld at the channel ensures a secure and reliable join.

According to one aspect of this disclosure, the welding pattern comprises a second welding zone at a first and a second longitudinal edge of the composite web so that the resulting pads have welded longitudinal edges which are more reliable than the glued edges of other solutions.

The two webs of non-woven fabric are joined by a permanent ultrasonic weld.

According to one aspect of this disclosure, the welding system is an ultrasonic welding system in which the first welding element is an anvil and the second welding element is a sonotrode acting on the anvil.

In one embodiment, the anvil is in the form of a welding roller comprising, on the outside surface of it, the opposing contact surface shaped according to the welding pattern.

According to one aspect of this disclosure, the welding roller is the forming drum which is thus provided with the opposing contact surface acted upon by the sonotrode.

The first welding element—for example a roller which acts as anvil and provided with the welding pattern—allows welding both the pad edges and the channels at the same time.

According to one aspect of this disclosure, the forming apparatus comprises a second welding system for welding the first web and the second web.

The second welding system comprises a third welding element and a fourth welding element acting in conjunction with each other.

The third welding element has a second opposing surface for contact with the fourth welding element and shaped according to a second welding pattern, different from the first welding pattern.

The second welding pattern comprises at least a second welding zone at the channel.

The first and second welding systems are used to weld absorbent pads of a first and second size, respectively, and operate alternatively; that makes the apparatus particularly versatile and capable of facilitating rapid changeovers to pads of different sizes.

The second welding system is preferably a microwave system; when there are two welding systems, the welding system that is not in operation merely constitutes a transit for the composite web.

According to one aspect of this disclosure, the gluing pattern comprises a zone which is free of adhesive, that is to say, without adhesive, at the channel.

In one embodiment, the welding pattern comprises a third welding zone transverse to the second welding zone to define a transverse end of the pad. That way, when the composite web is cut into pieces, the pads will be welded at the transverse edges as well as at the channels.

According to one aspect of this disclosure, the apparatus comprises a removal system for removing absorbent material and operating at the forming drum.

The removal system for removing the absorbent material is located downstream of the absorbent material spreader in the feed direction V of the first web to remove any absorbent material that may be present on the first web at the channel.

Removing the material that may be present there allows a better quality weld to be made, thus obtaining a more reliable pad.

In one preferred embodiment, the removal system for removing the absorbent material comprises a blowing system comprising at least one centrifugal impeller whose axis of rotation is parallel to the axis of rotation of the forming drum.

The impellers preferably have an outside surface which faces the forming drum.

According to one aspect of the disclosure, the outside surface of the impellers is at least partly radially aligned with the inserts where the channels are formed.

According to one aspect of the disclosure, the impellers generate a vortex at the inserts which forces any absorbent material that may be present there towards negative pressure zones of the forming drum.

In one embodiment, the removal system for removing the absorbent material may comprise a blow nozzle which may be, for example, oriented towards the forming drum in such a way as to blow away any absorbent material that may be present at the channel, on the first web.

According to one aspect of it, this disclosure relates to a method for forming an absorbent pad for an absorbent sanitary article of the kind described above.

The method comprises a step of feeding a first web intended to form the first layer of the pad, a step of feeding a second web intended to form the second layer of the pad, a step of spreading the absorbent material on the first web according to the above mentioned absorbent material spreading pattern, and a step of spreading an adhesive on the first web according to a gluing pattern.

Once joined to each other, the first web, the second web and the absorbent material form a composite web.

The method comprises a step of welding the first web and the second web, preferably ultrasound welding, according to a welding pattern comprising at least one welding zone at the channel.

According to one aspect of this disclosure, the method comprises a step of removing any absorbent material that may be present in the welding zone at the channel.

The step of removing the absorbent material comprises a step of blowing away any absorbent material that may be present in the welding zone at the channel.

BRIEF DESCRIPTION OF THE DRAWINGS

Further characteristics and advantages of this solution are more apparent in the non-limiting description below, with reference to a preferred but non-exclusive embodiment of a method and an apparatus for forming a pad, as illustrated in the accompanying drawings, in which.

DETAILED DESCRIPTION OF PREFERRED EMBODIMENTS OF THE INVENTION

Figure 1:
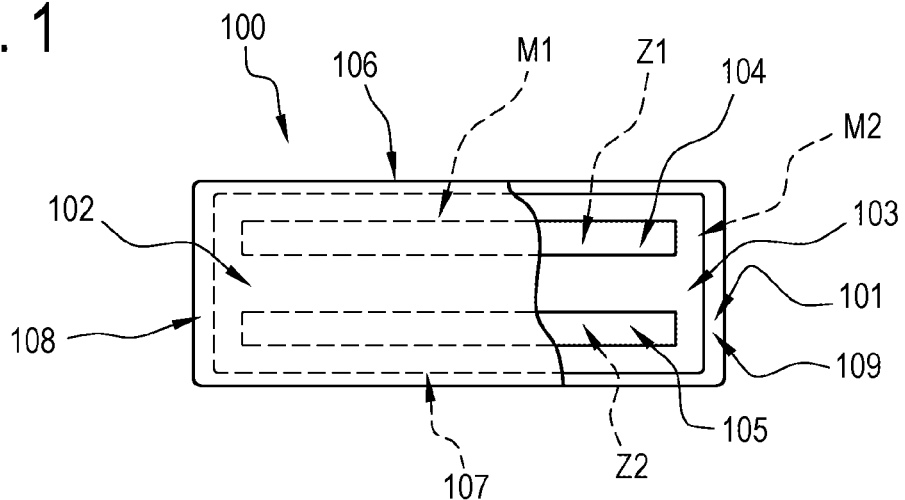
FIG. 1 is a schematic top plan view of an absorbent pad made by an apparatus according to this disclosure.

With reference to FIG. 1, the numeral 100 denotes a pad obtainable with a forming apparatus made in accordance with this disclosure.

The pad 100, intended for use in absorbent sanitary articles such as nappies for children or adults, for example, comprises a first layer 101, a second layer 102 and an absorbent material 103 interposed between the first and the second layer 101, 102 and arranged according to a spreading pattern M1.

The first and second layers 101, 102 are made, for example, of non-woven fabric and are joined to each other; the absorbent material 103 comprises, for example, cellulose fibres and superabsorbent material, also called SAP, and is fixed between the first and the second layer 101, 102.

In the example illustrated, the pattern M1, and hence the pad 100, has two zones or channels 104, 105 which are free of absorbent material and where the first and second layers 101, 102 are joined directly to each other.

In other words, the first layer 101 and the second layer 102 are directly attached to each other at the zones or channels 104, 105.

The involuntary presence of a minimum amount of absorbent material or anything else as a result, in particular, of the manufacturing process, may be considered absence of absorbent material.

In the preferred embodiment illustrated by way of example, the pad 100 has a first and a second longitudinal edge 106, 107 along which the first and second layers 101, 102 are joined directly to each other.

In the preferred embodiment illustrated by way of example, the pad 100 has a first and a second transverse edge 108, 109 along which the first and second layers 101, 102 are joined directly to each other.

Figure 2:
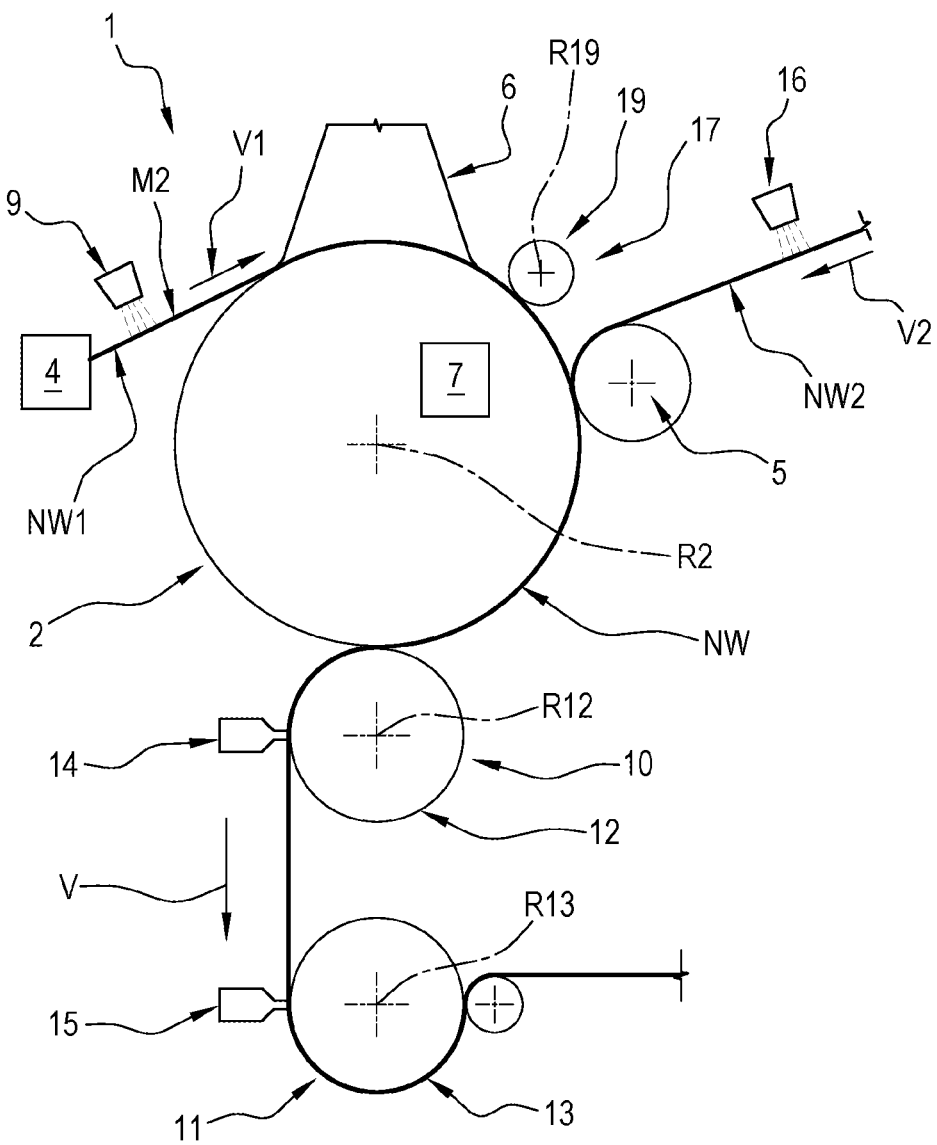
FIG. 2 is a schematic front view of a forming apparatus according to this disclosure for forming an absorbent pad.
Figure 3:
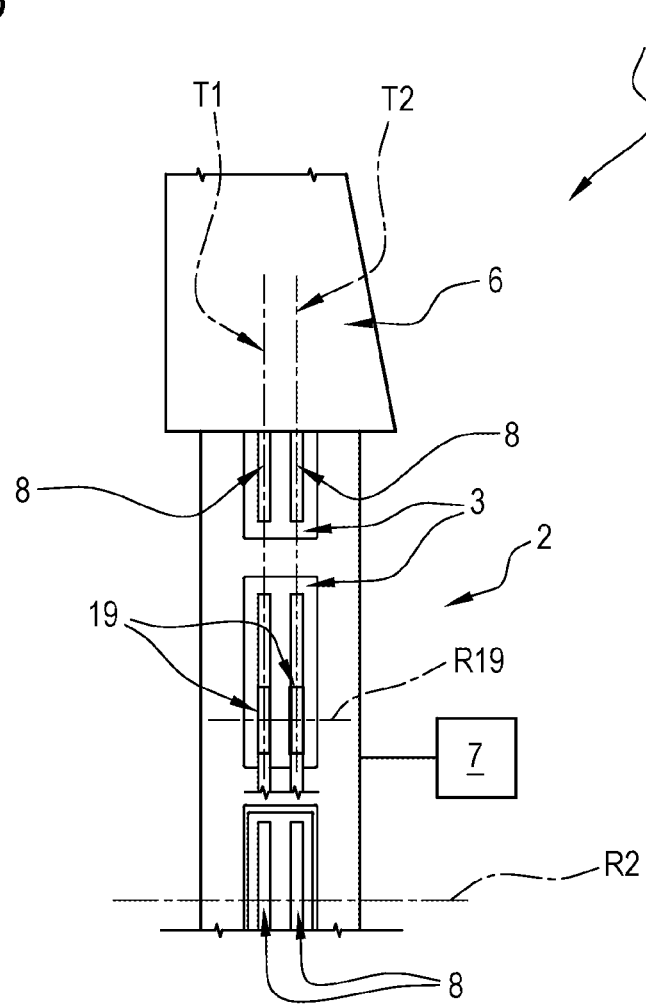
FIG. 3 illustrates the apparatus of FIG. 1 in a schematic front view, partly in blocks and with some parts cut away for greater clarity.
Figure 3:
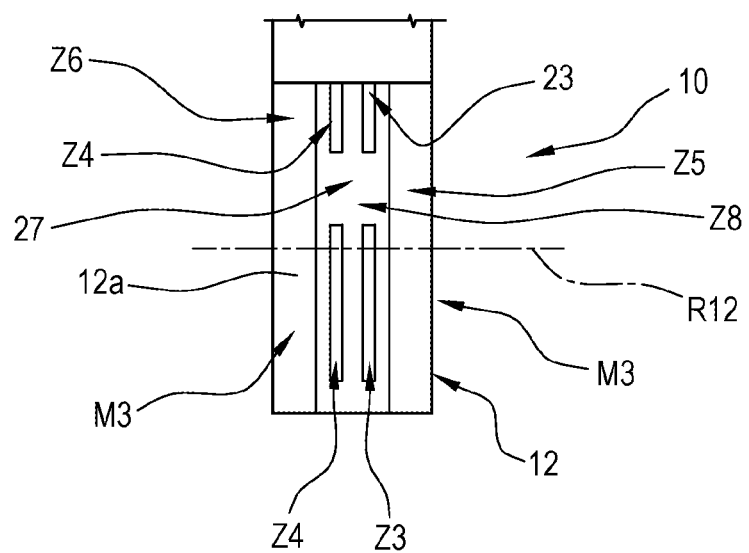

With reference to FIGS. 2 and 3, the numeral 1 denotes a forming apparatus for forming the pad 100 made in accordance with this disclosure.

This description of the apparatus 1 is limited to the parts necessary for understanding this invention.

The apparatus 1 comprises a drum 2 for forming the pads 100 and rotatable about an axis R2.

Along its periphery, the drum 2 comprises a plurality of seats 3, in particular for receiving the material 103, as described in more detail below.

The apparatus 1 comprises a first feed system, schematically represented as a block 4, for feeding a first web NW1 to the forming drum 2.

The web NW1 is movable in a direction V1 and is intended to form the first layer 101 of the pad 100.

The apparatus 1 comprises a second feed system, schematically represented as a block 5, for feeding a second web NW2 to the forming drum 2.

The web NW2 is movable in a direction V2 and is intended to form the second layer 102 of the pad 100.

The apparatus 1 comprises a spreader 6 for spreading the absorbent material 103 on the forming drum 2; the spreader 6 is of a substantially known type and is not described further.

The first web NW1, the second web NW2 and the absorbent material 103 together form a composite web NW.

The forming drum 2 comprises a suction system 7, schematically represented as a block, to create on the first web NW1 fed by the drum 2, a spread of absorbent material according to the absorbent material spreading pattern M1.

More specifically, the suction system 7 is in communication with the seats 3 which, in practice, are preferably suction tiles and which hold the material 103 at a predetermined position relative to the web NW1 according to the pattern M1.

The material 103 is positioned in the suction tiles which, in one embodiment, may be in the form of a continuous circular seat extending along a substantially cylindrical peripheral portion of the drum 2.

In another embodiment, of the type illustrated in the drawings, the suction tiles may be in the form of a plurality of discrete seats 3, aligned and equispaced along a substantially cylindrical peripheral portion of the drum 2.

The seats 3 may in any case be shaped to match the pad 100 and are capable of retaining by suction the absorbent material 103 transported by the drum 2.

As may be observed in particular in FIG. 3, the forming drum 2 comprises a plurality of inserts 8 in the suction system 7, positioned in particular in the seats 3, to inhibit suction at the channels 104 and 105 so that the absorbent material 103 is not retained on the web NW1 at the channels 104, 105.

In the preferred embodiment illustrated, the forming apparatus comprises an adhesive dispenser 9 located upstream of the spreader 6 of the absorbent material in the feed direction V1 to apply on the first web NW1 a layer of adhesive according to a pattern M2 for gluing the absorbent material 103.

In a preferred embodiment, the gluing pattern M2 corresponds to the absorbent material pattern M1, that is to say, the adhesive is applied on the web NW1 in the zones where the absorbent material 103 is to be deposited.

More specifically, the gluing pattern M2 comprises zones Z1, Z2 which are free of adhesive, corresponding to the channels 104, 105.

A preferred embodiment of the apparatus 1 comprises a welding system 10 to join the first and second webs NW1, NW2 according to a welding pattern M3.

In the preferred embodiment illustrated by way of example, the apparatus 1 comprises a welding system 10 to join the first and second webs NW1 and NW2 according to a welding pattern M3 and a welding system 11 to join the first and second webs NW1 and NW2 according to a welding pattern M4.

The systems 10 and 11 are used to weld pads 100 of different sizes and operate alternatively, that is to say, when the system 10 is operating, the web NW passes through the system 11 in transit only, and vice versa.

Preferably, the apparatus 1 comprises an ultrasonic welding system 10, 11.

The systems 10 and 11 each comprise a first welding element 12, 13 which, in the example illustrated, is defined by a welding roller rotatable about a respective axis of rotation R12, R13.

The systems 10 and 11 each comprise a second welding element 14, 15 which, in the example illustrated, is defined by a sonotrode.

The rollers 12 and 13 each define, for the respective sonotrodes, a welding anvil.

Each first welding element 12, 13 has an opposing surface for contact with the respective second welding element and shaped according to the respective welding pattern M3, M4.

The welding roller 12 with the respective welding pattern M3 is illustrated by way of an example in FIG. 3; the pattern M4 is conceptually identical to the pattern M3 and is therefore not described further.

The welding roller 12 has an opposing surface 12a for contact with the sonotrode 14 and shaped according to the respective welding pattern M3.

The pattern M3 comprises a welding zone Z3, Z4 corresponding to the channels 104, 105.

In practice, the surface 12a is shaped to define an anvil for the sonotrode 14 in the zones Z3, Z4 corresponding to the channels 104 and 105.

In a preferred embodiment of the apparatus 1, the pattern M3 comprises a welding zone Z5, Z6 at the longitudinal edges 106, 107 of the pad 100.

In practice, the surface 12a is shaped to define an anvil for the sonotrode 14 in the zones Z5, Z6 corresponding to the longitudinal edges 106 and 107 of the pad 100.

In an embodiment not illustrated, the pattern M3 comprises a welding zone Z7, Z8 at the transverse edges 108, 109 of the pad 100.

In practice, the surface 12a is shaped to define an anvil for the sonotrode 14 in the zones Z7, Z8 corresponding to the transverse edges 108 and 109 of the pad 100.

In an embodiment not illustrated, the welding roller, that is, the first welding element of the welding system 10, is the forming roller 2.

In such a case, the forming roller 2, which in the case of ultrasonic welding, constitutes the anvil of the system, comprises a respective opposing surface for contact with the sonotrode and shaped, for example, according to the welding pattern M3.

In the embodiment illustrated by way of example, the apparatus 1 comprises a second adhesive dispenser 16 for applying a layer of adhesive on the web NW2 in order to optimize to the first web NW1.

According to one aspect of this disclosure, the apparatus 1 comprises a removal system 17 for removing any absorbent material that may be present on the first web NW1 at the inserts 8, that is, in the zones of the web which will constitute the channels 104, 105.

The system 17 operates at the forming drum 2 and is mounted downstream of the spreader 6 of the absorbent material 103 in the feed direction V1 of the first web NW1.

In the embodiment illustrated by way of example, the removal system 17 for removing the absorbent material comprises a blowing system 18 which can blow away from the web NW1 any absorbent material 103 that may be present at the inserts 8, that is, at the channels 104 and 105. The material 103 may be blown onto the suction zones, where it is retained by the system 7.

According to one aspect of the disclosure, the blowing system 18 comprises at least one centrifugal impeller 19 whose axis of rotation R19 is parallel to the axis of rotation R2 of the drum 2; in the example illustrated, the system comprises two coaxial impellers 19, each disposed at a respective channel 104, 104.

In alternative embodiments, the blowing system comprises nozzles which blow air at the inserts 8 and which are preferably oriented towards the forming drum 2.

Preferably, the impellers 19, or the blowing nozzles, are disposed along the trajectories T1, T2 followed by the inserts 8 as the drum 2 rotates about the axis R2.

The impellers 19, or the blowing nozzles, are also optimized to prevent the blown air from modifying the pattern of the absorbent material 103 spread near the channels.

In alternative embodiments not illustrated, the removal system 17 for removing the absorbent material may, for example, comprise brushes acting on the web NW1 and/or a suction system for extracting the absorbent material and/or a scraper to ensure that the web NW1 remains clean at the channels 104, 105 where it will be welded.

According to one aspect of it, this disclosure has for an object a method for forming the absorbent pads 100 as described in the foregoing and illustrated in FIG. 1.

With reference, for example, to FIGS. 2 and 3, the method for forming an absorbent pad 100 comprises a step of feeding to the forming drum 2 the first web NW1, intended to form the first layer 101, a step of feeding to the forming drum 2 the second web NW2, intended to form the second layer 102, a step of spreading the absorbent material 103 on the first web NW1 according to the spreading pattern M1 and a step of spreading adhesive on the first web NW1 according to the gluing pattern M2.

According to one aspect of this disclosure, the method comprises a step of welding the first and second webs NW1, NW2, for example using ultrasound, according to the welding pattern M3 or M4, which comprises the welding zones Z3, Z4 at the channels 104, 105.

According to one aspect of this disclosure, the method comprises a step of removing any absorbent material 103 that may be present on the web NW1 in the welding zones Z3, Z4 where the channels 104, 105 will be defined.

In a preferred embodiment, illustrated by way of example, the step of removing the absorbent material 103 comprises a step of blowing away from the web NW1 any absorbent material 103 that may be present in the welding zones Z3, Z4 at the channels 104, 105 in order to clean the web so it is ready for subsequent welding.

Since the channels 104, 105 are not continuous along the composite web NW, and hence the zones 104, 105 free of absorbent material on the web NW1 are not continuous, the step of blowing is intermittent.

The invention claimed is:

1. An apparatus for forming an absorbent pad for an absorbent sanitary article, the absorbent pad comprising a first layer, a second layer and an absorbent material interposed between the first layer and the second layer and arranged according to an absorbent material spreading pattern including a channel free of absorbent material where the first layer and the second layer are joined directly to each other, the apparatus comprising:
   a forming drum,
   a first feed system for feeding a first web, configured to form the first layer, to the forming drum,
   a second feed system for feeding a second web, configured to form the second layer, to the forming drum,
   a spreader for spreading the absorbent material directly on the first web disposed on the forming drum, the forming drum comprising a suction system to create on the first web disposed on the forming drum a spread of absorbent material according to the absorbent material spreading pattern, the forming drum comprising an insert in the suction system to inhibit suction at the channel so that the absorbent material is not retained at the channel,
   the first web, the second web and the absorbent material together forming a composite web,
   a welding system for welding the first and second webs and comprising a first welding element and a second welding element acting in conjunction with each other,
   an adhesive dispenser located upstream of the spreader of the absorbent material in a feed direction of the first web to apply on the first web a layer of adhesive in a gluing pattern having at least a first zone with adhesive and at least a second zone which is free of the adhesive at the channel,
   wherein the first welding element includes a contact surface operatively engaging the second welding element and shaped according to a first welding pattern comprising a first welding zone at the channel, and
   a removal system configured for removing the absorbent material and located downstream of the absorbent material spreader in the feed direction of the first web to remove any absorbent material that is present on the first web at the channel,
   wherein the removal system comprises a blowing system comprising a centrifugal impeller having an axis of rotation parallel to an axis of rotation of the forming drum.

2. The apparatus according to claim 1, wherein the first welding pattern comprises a second welding zone at a first longitudinal edge and a second longitudinal edge of the composite web.

3. The apparatus according to claim 1, wherein the welding system is an ultrasound system, the first welding element being an anvil and the second welding element being a sonotrode acting on the anvil.

4. The apparatus according to claim 3, wherein the anvil is a welding roller comprising the contact surface shaped according to the first welding pattern.

5. The apparatus according to claim 4, wherein the welding roller consists of the forming drum.

6. The apparatus according to claim 1, and further comprising a second welding system for welding the first and second webs, a third welding element, and a fourth welding element acting in conjunction with each other, the third welding element including a second contact surface coming into contact with the fourth welding element and shaped according to a second welding pattern, the second welding pattern comprising a second welding zone at the channel, the first and second welding systems being configured to weld a first format and a second format of the absorbent pad.

7. The apparatus according to claim 1, wherein the first welding pattern comprises a third welding zone transverse to the second welding zone to define a transverse end of the absorbent pad.

8. The apparatus according to claim 1, wherein the removal system operates on the forming drum at the first welding zone.

9. The apparatus according to claim 1, wherein an outside surface of the centrifugal impeller faces the forming drum.

10. The apparatus according to claim 1, wherein the centrifugal impeller is at least partly aligned, in a radial direction, with the insert.

11. A method for forming an absorbent pad for an absorbent sanitary article, the absorbent pad comprising a first layer, a second layer and an absorbent material interposed between the first layer and the second layer and arranged according to a spreading pattern including a channel free of absorbent material where the first layer and the second layer are joined directly to each other, the method comprising:
providing:
a forming drum,
a first feed system for feeding a first web, configured to form the first layer, to the forming drum,
a second feed system for feeding a second web, configured to form the second layer, to the forming drum,
a spreader for spreading the absorbent material directly on the first web disposed on the forming drum, the forming drum comprising a suction system to create on the first web disposed on the forming drum a spread of absorbent material according to the absorbent material spreading pattern, the forming drum comprising an insert in the suction system to inhibit suction at the channel so that the absorbent material is not retained at the channel,
the first web, the second web and the absorbent material together forming a composite web,
a welding system for welding the first and second webs and comprising a first welding element and a second welding element acting in conjunction with each other,
an adhesive dispenser located upstream of the spreader of the absorbent material in a feed direction of the first web to apply on the first web a layer of adhesive, the adhesive dispenser providing a gluing pattern having at least a first zone with adhesive and at least a second zone which is free of the adhesive at the channel and wherein the first welding element includes a contact surface operatively engaging the second welding element and shaped according to a first welding pattern comprising a first welding zone at the channel, and
a removal system configured for removing the absorbent material and located downstream of the absorbent material spreader in the feed direction of the first web to remove any absorbent material that is present on the first web at the channel,
wherein the removal system comprises a blowing system comprising a centrifugal impeller having an axis of rotation parallel to an axis of rotation of the forming drum;
feeding the first web, to form the first layer;
feeding the second web, to form the second layer;
spreading the absorbent material on the first web according to the spreading pattern,
spreading the adhesive on the first web according to the gluing pattern comprising the zone which is free of the adhesive at the channel before the step of spreading the absorbent material on the first web, and
welding the first and second webs according to the first welding pattern comprising the first welding zone at the channel.

12. The method according to claim 11, and further comprising performing the welding step by ultrasound.

13. The method according to claim 11, and further comprising a step of removing any absorbent material that is present in the first welding zone of the first web at the channel.

14. The method according to claim 13, wherein the step of removing the absorbent material comprises a step of blowing away the absorbent material that is present in the first welding zone of the first web at the channel.

15. The method according to claim 14, wherein the blowing is intermittent.

* * * * *